(12) United States Patent
Harruna et al.

(10) Patent No.: US 7,411,053 B2
(45) Date of Patent: Aug. 12, 2008

(54) LIGAND-FUNCTIONALIZED/AZO COMPOUNDS AND METHODS OF USE THEREOF

(76) Inventors: Issifu I. Harruna, 3310 Waterford Way, Conyers, GA (US) 30012; Guangchang Zhou, 500 Northside Cir., NW., Apt. G3, Atlanta, GA (US) 30309

( * ) Notice: Subject to any disclaimer, the term of this patent is extended or adjusted under 35 U.S.C. 154(b) by 0 days.

(21) Appl. No.: 11/420,307

(22) Filed: May 25, 2006

(65) Prior Publication Data
US 2007/0276104 A1    Nov. 29, 2007

(51) Int. Cl.
C07D 519/00 (2006.01)
C07D 471/02 (2006.01)
C07D 401/04 (2006.01)
C07D 401/14 (2006.01)
C08F 4/04 (2006.01)

(52) U.S. Cl. .................. 534/751; 534/752; 526/147
(58) Field of Classification Search ................. 534/751, 534/752, 886
See application file for complete search history.

(56) References Cited

U.S. PATENT DOCUMENTS

| 3,956,269 | A | * | 5/1976 | Sheppard et al. ............ 534/886 |
| 4,910,264 | A | * | 3/1990 | Stapersma ............... 525/333.6 |
| 5,021,480 | A | * | 6/1991 | Ravichandran .............. 524/99 |
| 6,855,840 | B2 | | 2/2005 | McCormick et al. |
| 6,858,309 | B2 | | 2/2005 | Kambouris et al. |
| 6,911,510 | B2 | | 6/2005 | Lewandowski et al. |
| 6,919,409 | B2 | | 7/2005 | Charmot et al. |
| 6,936,670 | B2 | | 8/2005 | Kramer et al. |
| 6,949,613 | B2 | | 9/2005 | Haddleton |
| 6,962,961 | B2 | | 11/2005 | Lai |
| 6,967,228 | B2 | | 11/2005 | DeDecker et al. |
| 7,119,210 | B2 | * | 10/2006 | Schlueter .................... 548/260 |

FOREIGN PATENT DOCUMENTS

WO    WO-2004/062371    *    7/2004

OTHER PUBLICATIONS

Alkan et al., Synthetic Metals, 119(1-3), 133-134, 2001.*
Qiu et al., Chemical Abstracts, 122:291585, 1995.*
Synthesis and Characterization of Tris(2,2'-bipyridine)ruthenium(II)-Centered Polystyrenes via Reversible Addition-Fragmentation Chain Transfer (RAFT) Polymerization; Zhou, Guangchang and Harruna, Issifu I.; Macromolecules (2004), 37(19), 7132-7139.
Synthesis and Characterization of Bis(2,2':6',2"-terpyridine)ruthenium(II)-Connected Diblock Polymers via RAFT Polymerization; Zhou, Guangchang and Harruna, Issifu I.; Macromolecules, 38 (10), 4114-4123, 2005; Web Release Date: Apr. 12, 2005.

* cited by examiner

*Primary Examiner*—Fiona T Powers
(74) *Attorney, Agent, or Firm*—Gardner Groff Greenwald & Villanueva

(57) ABSTRACT

Described herein are ligand-functionalized/azo compounds and methods of use thereof.

5 Claims, 4 Drawing Sheets

US 7,411,053 B2

LIGAND-FUNCTIONALIZED/AZO COMPOUNDS AND METHODS OF USE THEREOF

ACKNOWLEDGEMENTS

The research leading to this invention was made with government support under Contract No. N00014-01-1-1042 awarded by the Department of the Navy, Office of Naval Research. The U.S. government may have certain rights in the invention.

BACKGROUND

Metal-containing polymers are attracting significant interest as these materials may combine the processability and mechanical properties of polymers with the unique optoelectronic properties of metal complexes. The development of metal-containing polymers with unique property profiles has been propelled by their potential use in diverse areas such as solar energy conversion, anti-corrosion, luminescent sensing, electroluminescence display, biotechnology, molecular machines, and molecular electronics. Thus, a number of metal-containing polymers, whose metal moiety is in either the polymer backbone or the side chain, have been reported in the literature. In particular, metal-containing polymers with well-defined architectures are currently under extensive investigation.

As polymerization has been utilized to construct new materials that serve to replace or improve naturally occurring materials, methods have been developed to control the parameters of the chemical processes used to produce the polymers. Control of these permits the preparation of polymers having specific technical requirements. Polymerization thermodynamics and kinetics are well understood and provide a wide array of options for conducting polymerization reactions, i.e., free radical polymerization reactions.

Currently, various polymerization techniques such as atom transfer polymerization (ATRP), ring-opening polymerization (ROP), nitroxide-mediated radical polymerization and reversible addition-fragmentation transfer (RAFT) are used for preparation of metal-containing macromolecules. However, both ATRP and ROP are successful only for a limited number of monomers and suffer from a number of disadvantages such as high reaction temperature and expensive reagents that are sometimes difficult to separate from the products. Moreover, RAFT polymerization can lead to colored polymers with long time consumption. Therefore, conventional free radical polymerization still possesses great potential from an industrial standpoint.

It is well known that an initiator plays an important role in radical polymerization since it determines the polymerization rate, the molecular weight, and other characteristics of polymers. Many ethylenically unsaturated monomers are polymerized by the use of free radical initiators, e.g., those having aliphatic azo or peroxide groups. However, the azo initiator is most commonly used because of its favorable kinetics of decomposition. Particularly, the functionality of the polymer chain ends derived from the used initiator can affect or alter the properties of the polymers.

Most synthetic approaches for the preparation of metal-containing polymers, however, have involved the construction of systems with broad molecular weight distributions and lack of control over polymer architecture. Therefore, it would, therefore, be desirable to provide a compound that is capable of initiating the polymerization of ethylenically unsaturated monomers to produce polymers having ligand terminal groups, which can subsequently complex with metal ions to form supramolecular materials.

SUMMARY

Described herein are ligand-functionalized/azo compounds and methods of use thereof. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

DETAILED DESCRIPTION

Figure 1:
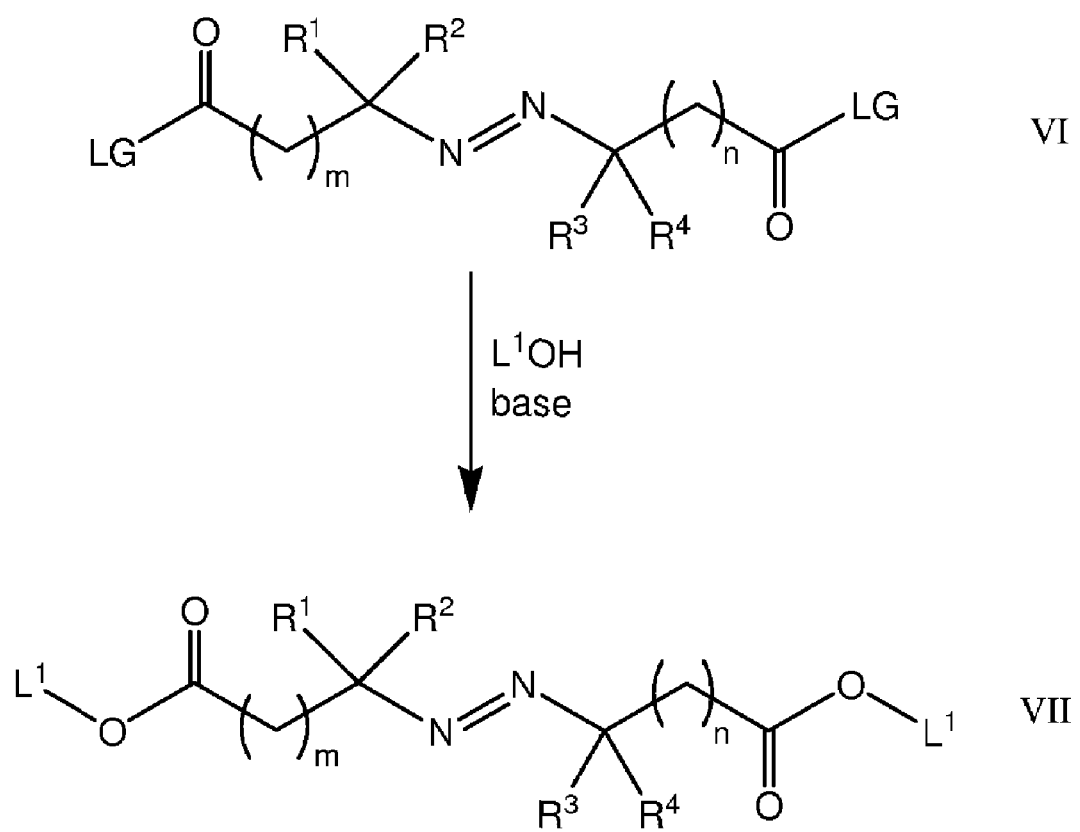
FIG. 1 shows an exemplary synthetic approach to produce ligand-functionalized/azo compounds.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

The term "independently" when referring to two or more particular R groups present in a formula refers to any combination of variables listed for that particular R group. For example, in the formula —NRR', where R and R' are, independently, hydrogen, methyl, or ethyl, any combination of R and R' is contemplated. Thus, for example, when R is hydrogen, R' can be hydrogen, methyl, or ethyl.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$, $R^2$, $R^3$, $R^4$, L, $L^1$, $L^2$, M, R, X, Y, Z, LG, m, n, and o used throughout the application are the same variables as previously defined unless stated to the contrary.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Additionally, if a generic formula has several variables, each and every combination of the variables in the formula is contemplated. For example, if an aryl ring is substituted with one or more $C_1$-$C_{15}$ alkyl groups, then every possible substitution about the aryl ring with respect to the different alkyl groups is contemplated.

I. Ligand-Functionalized/Azo Compounds and Preparation Thereof

Described herein are compounds useful in the polymerization of ethylenically unsaturated monomers to produce polymers comprising at least one ligand. In one aspect, the compound comprises at least one azo group and at least one ligand, wherein the ligand comprises at least one heteroaryl group or a heterocycloalkyl group.

The term "azo group" is defined herein as a moiety having the structure —N=N—.

The term "ligand" is defined herein as any group that can coordinate with a metal ion through a Lewis acid/base interaction. For example, the ligand can be a Lewis base and coordinate with a transition metal (Lewis base). Similarly, the ligand can be a Lewis acid as well that coordinates with a transition metal acting as a Lewis base. Alternatively, the ligand is capable of forming covalent bonds. For example, an amine can be deprotonated to form an amide, which can subsequently react with a transition metal to form a metal-amide complex.

The term "heteroaryl group" as used herein is an aromatic group that has at least one heteroatom incorporated within the ring of the aromatic group. Alternatively, the term "heteroaryl group" also covers aromatic groups that have one or more heteroatoms pendant or attached to the aromatic ring. Finally, the term "heteroaryl group" also covers aromatic groups that have one or more heteroatoms incorporated within the aromatic ring as well as one or more heteroatoms pendant or attached to the aromatic ring. Examples of heteroatoms include, but are not limited to, nitrogen, oxygen, sulfur, and phosphorus. The heteroaryl group can be substituted or unsubstituted. The heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy. It is contemplated that the heteroaryl group can be a fused system (e.g., 1,10-phenanthroline), or two or more heteroaryl groups attached to one another by one or more covalent bonds (e.g., bipyridine), or a combination thereof.

The term "heterocycloalkyl group" as used herein is a non-aromatic ring that has at least one heteroatom incorporated within the ring of the ring. Alternatively, the term "heterocycloalkyl group" also covers rings that have one or more heteroatoms pendant or attached to the non-aromatic ring. Finally, the term "heterocycloalkyl group" also covers rings that have one or more heteroatoms incorporated within the ring as well as one or more heteroatoms pendant or attached to the ring. Examples of heteroatoms include, but are not limited to, nitrogen, oxygen, sulfur, and phosphorus. The heteroaryl group can be substituted or unsubstituted. The heterocycloalkyl group can be substituted with one or more groups including, but not limited to, alkyl, alkynyl, alkenyl, aryl, halide, nitro, amino, ester, ketone, aldehyde, hydroxy, carboxylic acid, or alkoxy. It is contemplated that the heterocycloalkyl group can be a fused system, or two or more heterocycloalkyl groups attached to one another by one or more covalent bonds, or a combination thereof. It is also contemplated that one or aromatic groups can be fused to the heterocycloalkyl group.

With respect to the ligands, it is contemplated that there can be from one ligand present on the compound to a plurality of ligands. It is also contemplated that each ligands can have one or more Lewis acid or Lewis base groups capable of coordinating with another atom (e.g., a transition metal). For example, when the ligand is pyridine, the lone-pair electrons on the nitrogen atom can behave as Lewis base. Pyridine is a monodentate ligand, where only the lone-pair electrons of the lone nitrogen atom are capable of forming one Lewis acid/base interaction. When the ligand is bipyridine, two nitrogen atoms with lone-pair electrons are available as Lewis bases. Bipyridine is referred to as a bidentate ligand. If the ligand possesses three groups that can behave as a Lewis acid or base, it is a tridentate ligand. If two or more ligands are present on the compound, they can be the same or different. In one aspect, the compound comprises two ligands. In another aspect, the compound comprises two ligands, wherein each ligand is bidentate or each ligand is tridentate.

In one aspect, the ligand is a heteroaryl group, wherein the heteroaryl group comprises at least one oxygen atom, sulfur atom, or phosphorous atom. Examples of such ligands include, but are not limited to, substituted aromatic compounds (e.g., Ar—X, where X is OH, alkoxy, SH, S-alkyl, $PH_2$, or P-alkyl$_2$).

In another aspect, the ligand is a heteroaryl group, wherein the heteroaryl aryl group comprises at least one nitrogen atom. In one aspect, the ligand is a heteroaryl group, wherein the ligand comprises two or three nitrogen atoms. In another aspect, the compound comprises two ligands, wherein each ligand comprises two or three nitrogen atoms. In one aspect, the heteroaryl group comprises a bipyridine group, a tripyridine group, or a phenanthroline group. In another aspect, the heteroaryl group comprises

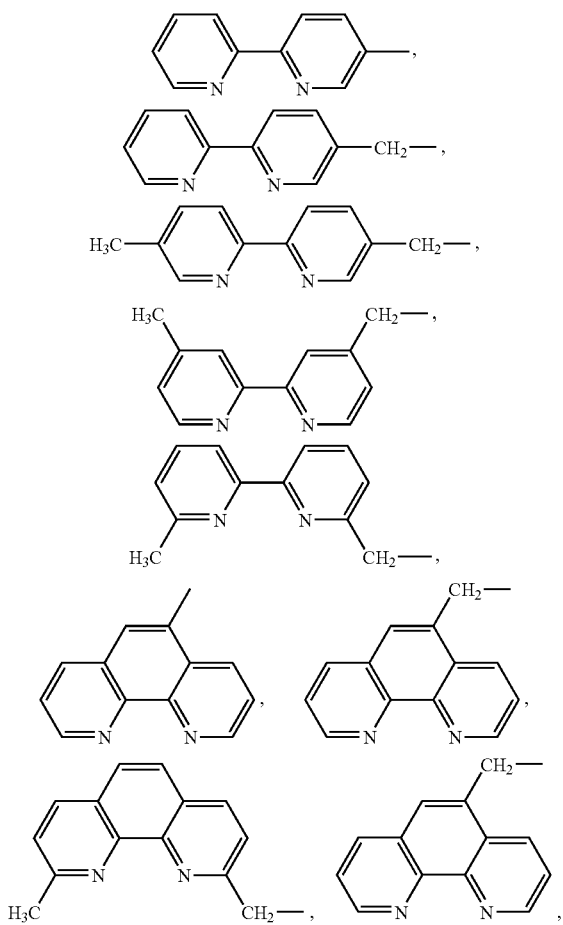

SCHEME 1

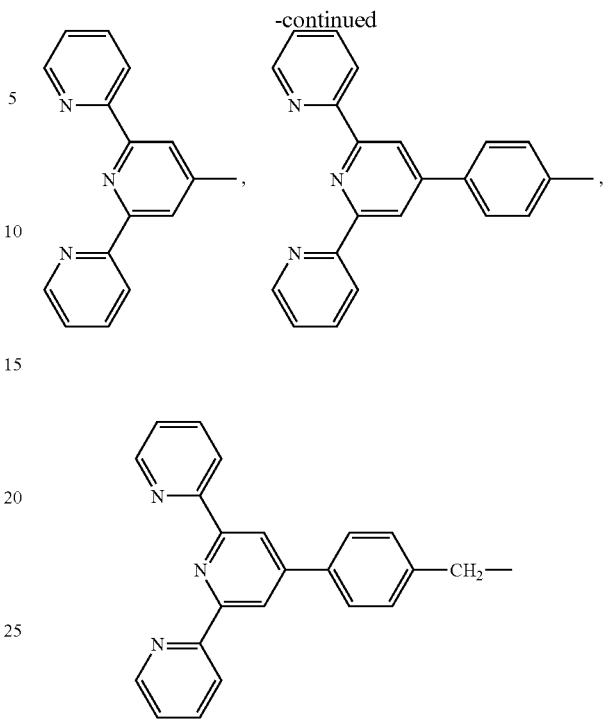

It is also contemplated that the heteroaryl group can be an aniline (substituted or unsubstituted) or bis-aniline, where the amino group is pendant to the aromatic ring.

As with heteroaryl groups, heterocycloalkyl groups can be monodentate or multidentate (e.g., bi- or tridentate). Examples of heterocycloalkyl groups are depicted in formula V,

V where Z is O, S, NR, or PR (R is hydrogen or alkyl) and o is an integer from 1 to 7. It is also contemplated that the heterocycloalkyl group can have one or aromatic rings fused to the heterocycloalkyl group (e.g., 2,3-dihydroindole). Examples of heterocycloalkyl groups include, but are not limited to, tetrahydrofuran, tetrahydrothiophene, tetrahydropyrrole, or morpholine.

In one aspect, the ligand-functionalized/azo compound comprises at least one electron-withdrawing group covalently attached to the compound. The term "electron-withdrawing group" as used herein is defined as a group that has an affinity for electron density (i.e., affinity to be electronegative). Examples of electron-withdrawing groups include, but are not limited to, $NR_3^+$, $SR_2^+$, $NH_3^+$, $NO_2$, $SO_2R$, CN, $SO_2Ar$, or halides, where R is an alkyl group and Ar is an aryl group. The location of the electron-withdrawing group in the compound can vary. In one aspect, the electron-withdrawing group (EWG) is present on the carbon attached to the azo group (e.g., N=N—C-EWG). In one aspect, the ligand-functionalized/azo compound comprises one or two cyano groups.

In one aspect, the ligand-functionalized/azo compound comprises the formula I

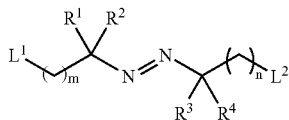

wherein $L^1$ and $L^2$ are, independently, a heteroaryl group or a heterocycloalkyl group;
$R^1$, $R^2$, $R^3$, and $R^4$ are, independently, an alkyl group, or an electron-withdrawing group; and
m and n are, independently, an integer greater than 1.

The term "alkyl group" as used herein is a branched or straight chain saturated hydrocarbon group of 1 to 15 carbon atoms, such as methyl, ethyl, n-propyl, isopropyl, n-butyl, isobutyl, t-butyl, pentyl, hexyl, heptyl, octyl, decyl, or tetradecyl, and the like. A "lower alkyl" group is an alkyl group containing from one to six carbon atoms.

The value of m and n in formula I can be 1, 2, 3, 4, 5, 6, 7, 8, or 9.

In another aspect, the ligand-functionalized/azo compound comprises the formula II

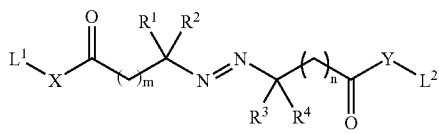

wherein $L^1$ and $L^2$ are, independently, a heteroaryl group;
$R^1$ and $R^3$ are a $C_1$-$C_4$ alkyl group;
$R^2$ and $R^4$ are a cyano group;
X and Y are, independently, O or NH; and
m and n are 2 or 3.

In one aspect, when the compound has the formula II, $L^1$ and $L^2$ are, independently, a bipyridine group, a tripyridine group, or a phenanthroline group. In another aspect, when the compound has the formula II, $L^1$ and $L^2$ are, independently, the ligands depicted in Scheme 1.

In another aspect, the ligand-functionalized/azo compound has the formula III

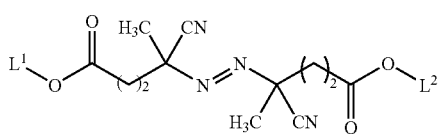

wherein $L^1$ and $L^2$ are

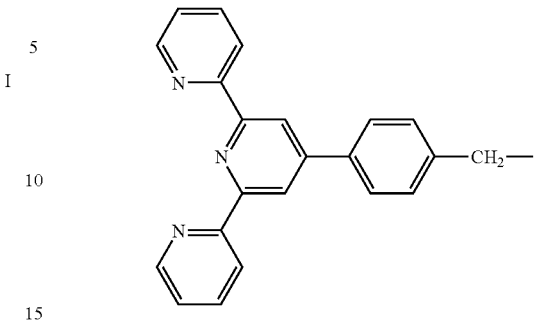

In a further aspect, the ligand-functionalized/azo compound has the formula IV

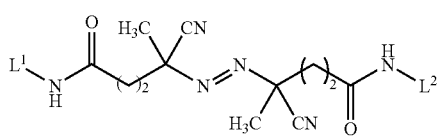

wherein $L^1$ and $L^2$ are

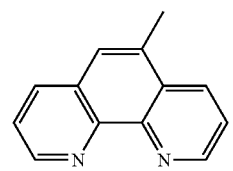

Figure 2:
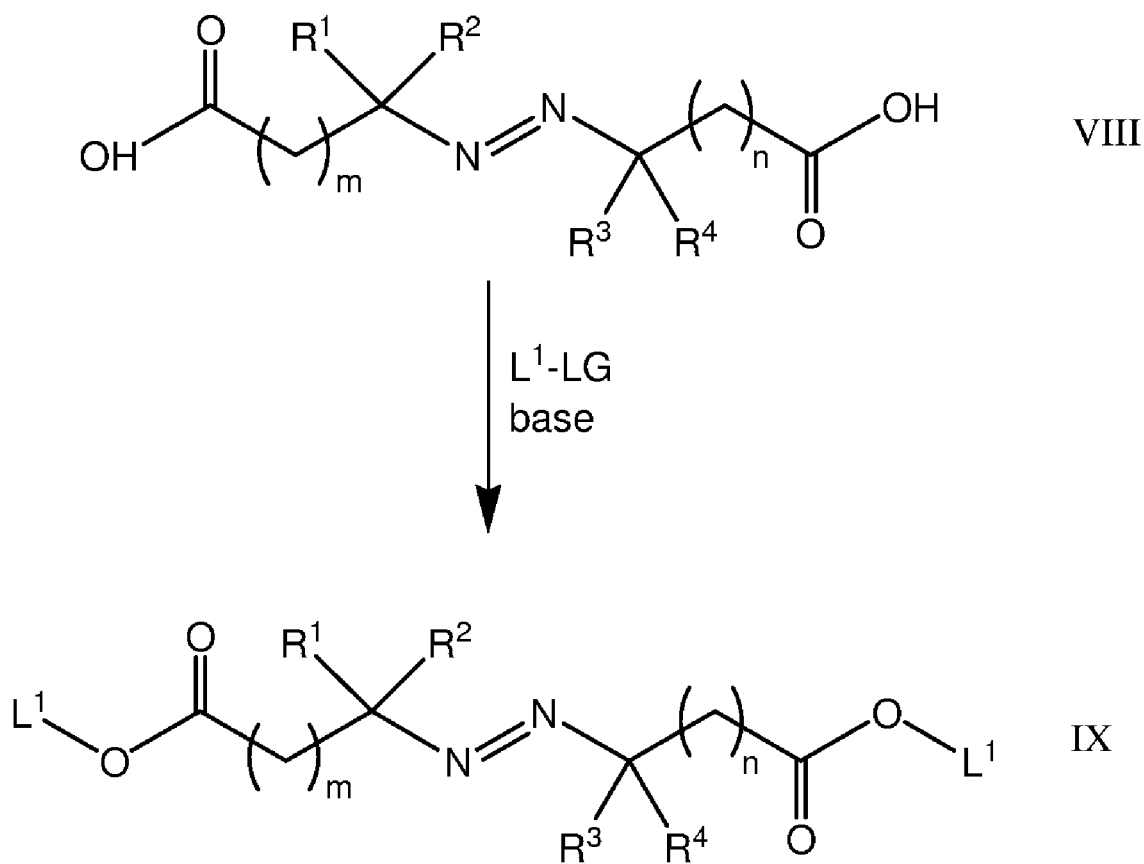
FIG. 2 shows another exemplary synthetic approach to produce ligand-functionalized/azo compounds.

The ligand-functionalized/azo compounds described herein can be prepared using techniques known in the art. One synthetic approach is depicted in FIG. 1. In this aspect, compound VI, where $R^1$-$R^4$, m, and n are defined as above and LG is a leaving group such as chloride, bromide, or alkoxy group, is reacted with an alcohol $L^1$OH in the presence of a base to produce the ester VII. It is also contemplated that $L^1NH_2$ can also be reacted with compound VI to produce an amide. Another approach is depicted in FIG. 2, where the dicarboxylic acid VIII is reacted with $L^1$-LG, where $L^1$ and LG are defined as above, in the presence of a base to produce compound IX. It is also contemplated that the diamide of compound VIII can also be used as well.

II. Methods of Use

The compounds described herein can be used to produce polymers having one or more ligands. In one aspect, described herein are methods for producing a polymer, wherein the method comprises heating a mixture of one or more ethylenically unsaturated monomers and one or more ligand-functionalized/azo compounds described herein.

The term "ethylenically unsaturated monomer" is defined herein as compound having at least one carbon double or triple bond. In one aspect, the ethylenically unsaturated monomer comprises an alkylacrylate, a methacrylate, an acrylate, an alkylacrylamide, a methacrylamide, an acrylamides, a styrene, an allylamine, an allylammonium, a diallylamine, a diallylammonium, an n-vinyl formamide, a vinyl ether, a vinyl sulfonate, an acrylic acid, a sulfobetaine, a carboxybetaine, a phosphobetaine, or maleic anhydride.

Examples of ethylenically unsaturated monomers include, but are not limited to, methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimiide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylbiphenyl, vinylanisole, vinylimidazolyl, vinylpyridinyl, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, and octadecyl methacrylate.

The polymerization can occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, methylene chloride, ether (e.g., diethyl ether), chloroform, and ethyl acetate. In one aspect, the solvent includes water, and mixtures of water and water-miscible organic solvents such as DMF.

The ligand-functionalized/azo compounds described herein upon heating produce radicals upon heating. Referring to Scheme 2 below, upon heating the ligand-functionalized/azo compound having the formula $L^1$-N=N-$L^1$, the radical $L^1 \cdot$ is produced, where $L^1$ can be any ligand described herein. The radical then reacts with the ethylenically unsaturated monomer M to produce a living polymer $[L^1\text{-}(M)_{n-1}\text{-}M \cdot]$ by free radical polymerization. The polymerization is then terminated when the living polymer reacts with a second equivalent of $L^1$.

SCHEME 2

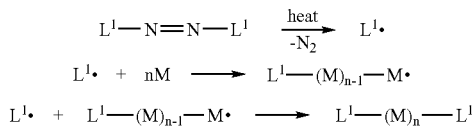

The temperature and duration of heating will vary depending upon the selection of the ligand-functionalized/azo compound and the ethylenically unsaturated monomer. Similarly, the amount of the ligand-functionalized/azo compound can also vary.

In one aspect, a chain transfer agent (CTA) is used in combination with the ligand-functionalized/azo compounds described herein during the polymerization process. Chain transfer agents have been used in reversible addition-fragmentation (RAFT) polymerizations. In one aspect, the chain transfer agent is a thiocarbonylthio compound. Any of the chain transfer agents disclosed in U.S. Pat. No. 6,855,840, which is incorporated by reference in its entirety, can be used herein. In one aspect, the chain transfer agent comprises the formula X,

where Ph is a phenyl ring and L is any ligand described herein.

When the chain transfer agent is used in combination with the ligand-functionalized/azo compound, a number of different polymers can be produced. Scheme 3 below depicts some of the polymers that can be produced upon the polymerization of the ethylenically unsaturated monomer M.

SCHEME 3

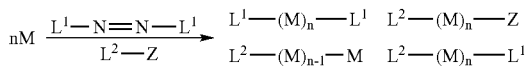

Referring to Scheme 2, the chain transfer agent is denoted as $L^2$-Z, where $L^2$ is any ligand described herein and Z is a group capable of forming a radical (e.g., thiocarbonylthio compound). It is contemplated that $L^1$ and $L^2$ can be the same or different ligand; however, in certain aspects, it is desirable that $L^1$ and $L^2$ be the same ligand. In one aspect, when the ligand-functionalized/azo compound has an electron-withdrawing group (e.g., a cyano group), the resultant polymer also possesses an electron-withdrawing group. Scheme 3 depicts some of the polymerization products. It is contemplated that the polymers can be terminated with a variety of different ligands and groups. Using techniques known in the art, it is possible to characterize and isolate the different polymeric species. The Examples below provide additional information as to the production, isolation, and characterization of the ligand terminated polymers.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Di-[4-(2,2':6',2")terpyridin-4'-yl-benzyl]-4,4'-azobis(4-cyanovalerate) (TPY-AIBN)

A reaction mixture of 4'-(4-bromomethylphenyl)-2,2':6', 2"-terpyridine (1.500 g, 3.729 mmol), 4,4'-azobis(4-cyanopentanoic acid) (500 mg, 1.7839 mmol), $Cs_2CO_3$ (750 mg, 2.302 mmol), 1.0 ml of water and 100 ml of acetone was stirred vigorously at room temperature for 5 days. The solvents were removed under vacuum, and $CH_2Cl_2$ was added. The precipitate was filtered off. The filtrate was evaporated to dryness under vacuum, and then 300 ml of $CH_2Cl_2$-hexane mixture solvents (1:12, v/v) was added. The precipitate was filtered, and dried, and further purified by column chromatography ($Al_2O_3$) using ethyl acetate-hexane (3:2, v/v) as eluent to give pure product (0.763 g, 46%). $^1$H-NMR ($CDCl_3$): δ=8.64 (m, 12H), 7.85 (m, 8H), 7.47 (m, 4H), 7.30 (m, 4H), 5.20 (s, 4H, —$CH_2$—O—C(O)—), 2.65-2.48(m, 8H, —OOC—$CH_2CH_2$—), 1.69(m, 6H, =N—C(CN)—$CH_3$). HRMS (TOF): calculated for $C_{56}H_{47}N_{10}O_4[(M+H)^+]$ m/z=923.3782, found m/z=923.3759 Fluorescent Spectral Properties: $\lambda_{ex}$=320 nm, $\lambda_{em}$=380 nm.

Example 2

Preparation of Di-[(1,10)phenanthrolin-5-yl]-4,4'-azobis(4-cyanovaleramide)

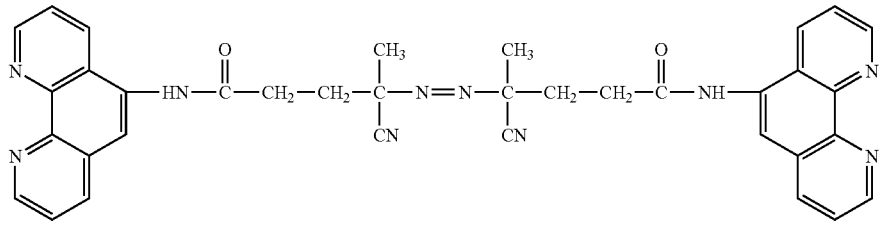

A. Preparation of 4,4'-Azobis(4-cyanopentanoic acid chloride)

A 14 g (50.0 mmol) sample of 4,4'-Azobis(4-cyanopentanoic acid) was carefully added to a suspension of 52.0 g (249.7 mmol) of $PCl_5$ in 100 ml of $CH_2Cl_2$ under ice cooling. The reaction mixture was warmed to room temperature and stirred overnight. Excess $PCl_5$ was filtered off. The volume was reduced to 20% by evaporating $CH_2Cl_2$, whereby more $PCl_5$ precipitated as a yellow solid, which again was filtered off. The product was isolated by slowly pouring the filtrate into 150 ml of ice-cold n-hexane, filtering off, washing with ice cold n-hexane, and drying in a vacuum, yield 11.70 g target product. $^1$H-NMR ($CDCl_3$): δ=3.18-3.00 (m, 4H,

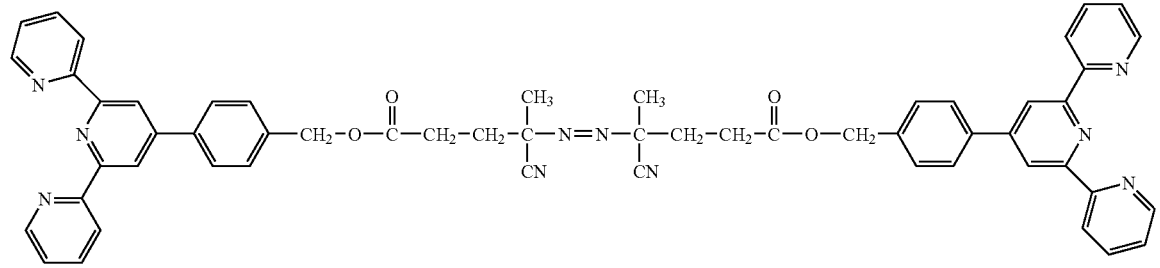

CH$_2$CO), 2.60-2.46 (m, 4H, CH$_2$C), 1.76 and 1.69 (s each, 6H total, CH$_3$). $^{13}$C-NMR (CDCl$_3$): δ=172.1, 116.8, 71.3, 41.6, 32.9, 23.5.

B. Preparation of 1,10-Phenanthroline-5-amine

This compound was synthesized by the reduction of 5-nitro-1,10-phenanthroline. The procedure was manipulated under argon. To a suspension of 5-nitro-1,10-phenanthroline (2.06 g, 9.0 mmol) and 10% Pd/C (0.280 g) in 90 ml of 95% EtOH, hydrazine hydrate (2.0 ml, 42 mmol) was added dropwise. The mixture was heated for 3 h at 70° C. and then filtered hot through a glass-fiber filter to remove the catalyst. The yellow solution was concentrated to 25 ml and left at 4° C. for 24 hours. The precipitate was filtered off, washed with cold Et$_2$O, and dried under vacuum for 24 hours to give 1.425 g of product (81%). $^1$H-NMR (DMSO-d$_6$): δ=9.08 (m, 1H), 8.71 (m, 2H), 8.06 (m, 1H), 7.75 (q, 1H), 7.52 (q, 1H), 6.90 (s, 1H), 6.17 ppm (d, NH$_2$). $^{13}$C-NMR (DMSO-d$_6$): δ=149.3, 146.2, 144.8, 142.7, 140.5, 132.7, 130.8, 123.2, 122.0, 101.8 ppm.

C. Preparation of Di-[(1,10)phenanthrolin-5-yl]-4,4'-azobis(4-cyanovalerylamide)

A 500-ml two-necked flask fitted a reflux condenser was charged with 607 mg (3.109 mmol) of 1,10-phenanthroline-5-amine, dried methylene chloride (160 ml) and dried THF (80 ml). The mixture was heated until the complete dissolution of 1,10-Phenanthroline-5-amine, and then cooled to room temperature. After removal of the condenser, dried triethylamine (0.60 ml) was added to the cooled solution, and followed the dropwise addition of a solution of 4,4'-azobis(4-cyanopentanoic acid chloride) in 30 ml of CH$_2$Cl$_2$-THF (2:1, v/v) mixture solvents under stirring. The resulting mixture was continuously stirred under argon for 72 hours. All solvents were removed under reduced pressure, and then water was added. The resulting mixture was adjusted to pH 8 with 1% NaOH solution, and stirred at room temperature overnight. The precipitate was collected by centrifugation separation, and dried in an oven with P$_2$O$_5$ under vacuum. The dried precipitate was washed with CH$_2$Cl$_2$ to give crude product. The crude product was dissolved in MeOH—CHCl$_3$ (1:5, v/v) mixture solvents to a solution. The solution was added dropwise into excess acetone-hexane (1:1, v/v) mixture solvents, and the precipitate was collected by centrifugation separation to give pure product (136 mg, 23%). $^1$H-NMR (CDCl$_3$—CD$_3$OD, 5:2): δ=8.97 (q, 4H), 8.37 (d, 2H), 8.00 (d, 2H), 7.93 (s, 2H), 7.50 (m, 4H), 2.87-2.54 (m, 8H), 1.80 (s, 6H). HRMS (TOF): calcd for C$_{36}$H$_{31}$N$_{10}$O$_2$[(M+H)$^+$] m/z=635.2631, found m/z=635.2592 Fluorescent Spectral Properties: λ$_{ex}$=345 nm, λ$_{em}$=400 nm.

Example 3

Polymerization Reactions

Materials 2,2'-Azobis(isobutyronitrile) (AIBN, 97%, Aldrich) was purified by recrystallization from methanol and stored in a freezer. Styrene (99%, Aldrich) was purified by washing with an aqueous solution of NaOH (5 wt %) to remove inhibitor, followed by distilled water until the washings were neutral to litmus and fractionally distilled under vacuum. CTA1 was synthesized according to the procedure described previously. CTA2 and the initiator TPY-AIBN was synthesized using the techniques described in Example 1.

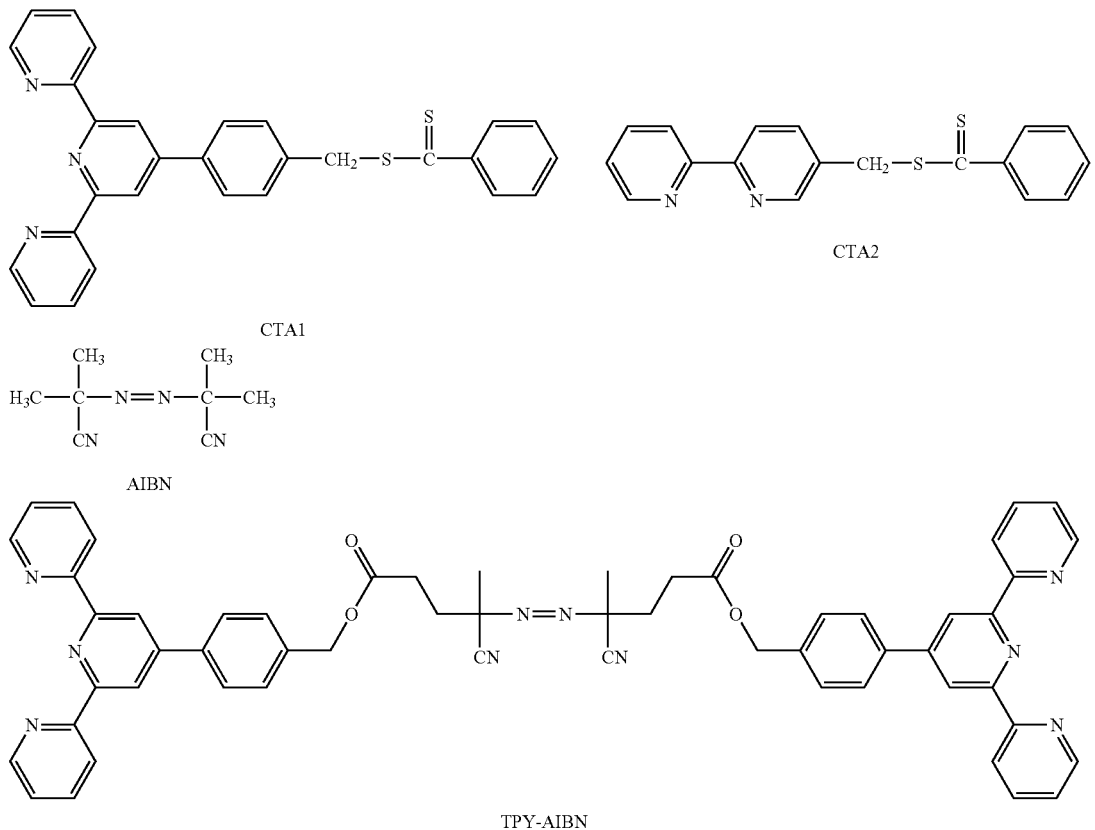

Characterization

¹H and ¹³C nuclear magnetic resonance (NMR) spectra were recorded on a Bruker ARX400 spectrometer at 400 Hz and 100 MHz, respectively. Size exclusion chromatography (SEC) was carried out on a Viscotek SEC assembly consisting of a model P1000 pump, a model T60 dual detector, a model LR40 laser refractometer and three mixed bed columns (pore size: 10 μm, the molecular weight range for those columns is 1,000-5,000,000) from America Polymer Standards Corporation using THF as an eluent with a flow rate of 1.0 mL min⁻¹ at ambient temperature. Polymer concentrations for SEC experiments were prepared in concentrations of about 3.0 mg/mL. The SEC system was calibrated using a narrow polystyrene standard ($M_n$=9870, $M_w$=10300, $M_p$=10300, $M_w/M_n$=1.04). As routine analysis, MALDI-TOF-MS was performed using 1,8-dihydroxy-9(10OH)-anthracenone (dithranol) or α-cyano-4-hydroxycinnamic acid as a matrix in the absence of cationic agents in the Mass Spectrometry Laboratory of Georgia Institute of Technology, Atlanta, USA.

RAFT Polymerization of Styrene

Styrene (2.660 g, 25.54 mmol), TPY-AIBN (22.0 mg, 2.38×10⁻² mmol) and CTA1 (56.0 mg, 1.18×10⁻¹ mmol) were mixed to give a clear solution. The solution was transferred into an ampule and degassed through five freeze-thaw-evacuate cycles, sealed under vacuum, and heated at 65° C. for 6 h. The polymerization mixture was poured into a large excess of methanol to precipitate the resulting polymer. The polymer was purified by reprecipitation three times from 1,4-dioxane into a large excess of methanol, and then dried under vacuum at room temperature to yield 0.240 g of a pink polymer PS-1. The conversion of the monomer styrene was determined to be 6.9% by gravimetrical method.

PS-2 was similarly prepared as described above using the following reagent loadings. Styrene (2.660 g, 25.54 mmol), AIBN (4.0 mg, 2.44×10⁻² mmol) and CTA2 (38.0 mg, 1.18×10⁻¹ mmol). Polymerization time: 5 h. Yield: 0.158 g, Conversion: 4.5%.

The two RAFT-prepared polystyrene polymers, PS-1 and PS-2, were characterized by both ¹H and ¹³C NMR techniques. Their ¹H-NMR spectra both show the appearance of signals located at 4.60-5.20 and 7.84 ppm attributed to the proton of the methine group adjacent to the sulfur and aromatic protons of the active end group (Ph-C(=S)—S—) from the RAFT agent, CTA1 and CTA2, respectively. The existence of the active Ph-C(=S)—S— group at one end of the polymer chain was further confirmed by the appearance of two signals located at 52.40-54.00 and 226.04 ppm assigned to the backbone CH carbon next to sulfur and the C=S carbon, respectively, in their ¹³C-NMR spectra. Terpyridine and bipyridine functional endgroups derived from RAFT agents, CTA1 and CTA2, were also present in their corresponding polystyrene polymers as observed by their characteristic peaks in ¹H- and ¹³C-NMR spectra.

The molecular weights and molecular weight distributions of the two polystyrene polymers were determined by SEC to be $M_n$=3340 g/mol; $M_w/M_n$=1.09 for PS-1, and $M_n$=2080 g/mol; $M_w/M_n$=1.10 for PS-2. Their ¹H-NMR-determined molecular weights ($M_n$=2230 g/mole for PS-1 and 1470 g/mol for PS-2) are in good agreement with theoretically calculated values ($M_n$=2040 g/mole for PS-1 and 1340 g/mol PS-2).

Figure 3:
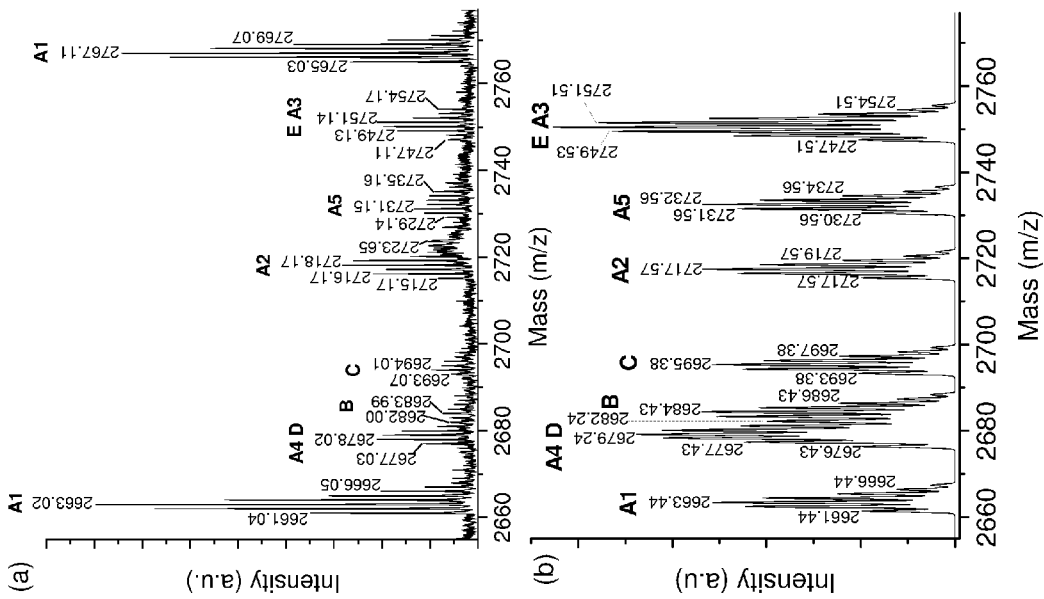
FIG. 3 shows the expanded MALDI-TOF-MS spectrum of the RAFT-prepared polystyrene PS-1 (a) and the theoretical monoisotopic distributions of each actual cluster (b).
Figure 4:
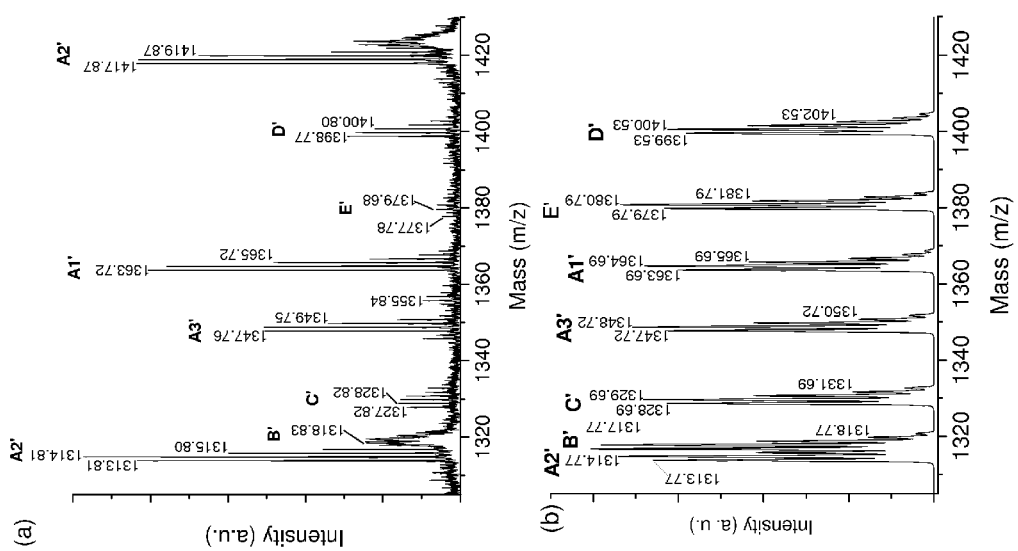
FIG. 4 shows the expanded MALDI-TOF-MS spectrum of the RAFT-prepared polystyrene PS-2 (a) and the theoretical monoisotopic distributions of each actual cluster (b).

The two RAFT-prepared polystyrene polymers, PS-1 and PS-2, were further analyzed by MALDI-TOF-MS technique. Their expanded MALDI-TOF-MS spectra are shown in FIGS. 3a and 4a, with theoretical monoisotropic distributions of each cluster in FIGS. 3b and 4b. Several series peaks are observed, all corresponding to a molar mass distribution of polystyrene with 104.15 u between the peaks. For a given series and a given degree of polymerization, the multiplicity of the peak corresponds to the isotopic distribution, which is a function of the various atoms existing in the structure, including the proton. However, some unexpected polymer chain endgroups were produced during the course of the MALDI-TOF-MS analysis. For example, the Ph-C(=S)—S-terminated polystyrene chains were promptly fragmented to produce vinyl endgroups (Equation 1 in Scheme 4). Since evidence of unsaturation is not seen in the ¹H-NMR data, it is therefore proposed that this species is produced within the mass spectrometer. The loss of HS—C(=S)—Ph in such a manner is a known fragmentation route in MS due to the weakness of the C—S bond between the polymer chain and dithiobenzoate chain end.

SCHEME 4

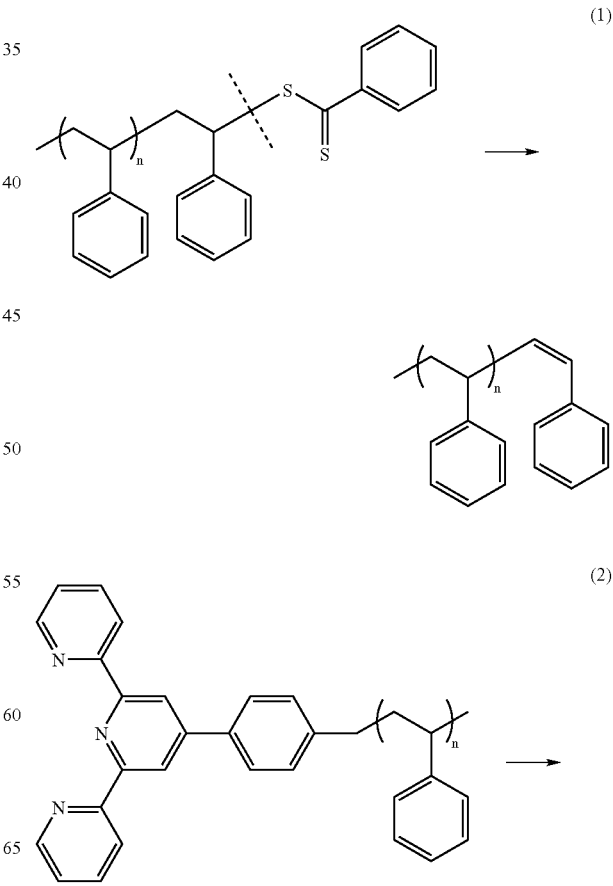

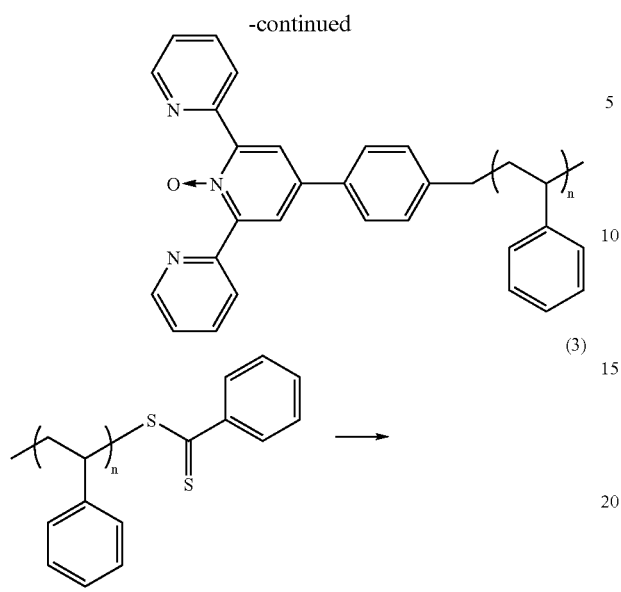

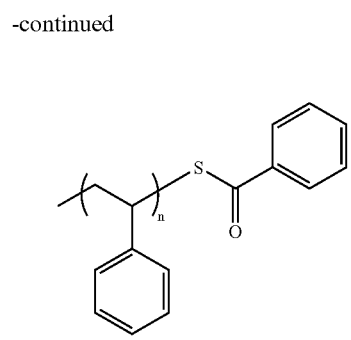

In addition to the occurrence of fragmentation, the terpyridine and dithiobenzoate end groups were also oxidized during the MALDI process (Equations 2 and 3 in Scheme 4). Considering that the three types of side-reactions originated from MALDI itself, we elucidated the two MALDI-TOF-MS spectra shown in FIGS. 3a and 4a and summarized the results in Tables 1 and 2.

TABLE 1

Assignment of peaks in the MALDI-TOF-MS spectrum (FIG. 3a) of the RAFT-prepared polystyrene PS-1 obtained using dithranol as a matrix in absence of cationic agents: calculated molar mass of the monoisotopic peak (first peak of the isotopic distribution) for the various possible structures and comparison with the experimental values.

| Peak | Structure | n | molar mass of the monoisotopic peak (u) Calcd | Exptl |
|---|---|---|---|---|
| A1 | 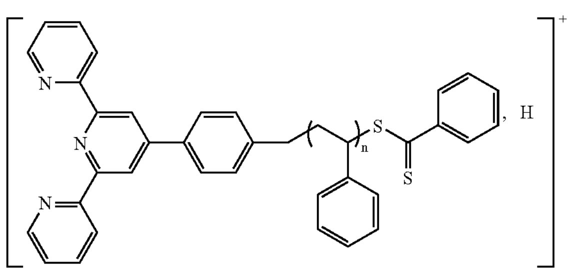 | 21 | 2661.44 | 2661.04 |
| A2 | 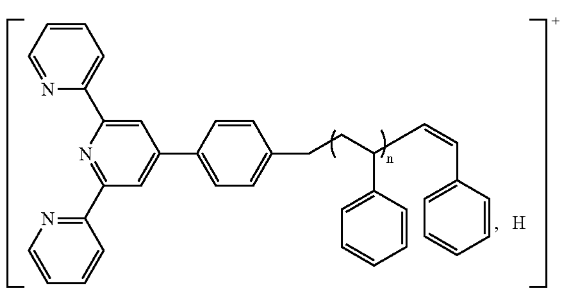 | 22 | 2715.57 | 2715.17 |

TABLE 1-continued

Assignment of peaks in the MALDI-TOF-MS spectrum (FIG. 3a) of the RAFT-prepared
polystyrene PS-1 obtained using dithranol as a matrix in absence of cationic agents: calculated
molar mass of the monoisotopic peak (first peak of the isotopic distribution)
for the various possible structures and comparison with the experimental values.

| Peak | Structure | n | molar mass of the monoisotopic peak (u) | |
|------|-----------|---|-------|-------|
|      |           |   | Calcd | Exptl |
| A3   | 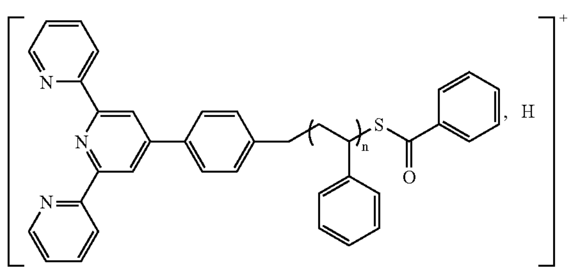          | 22 | 2749.53 | 2749.13 |
| A4   | 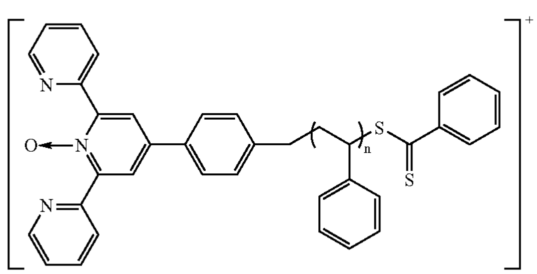          | 21 | 2676.43 | 2677.03 |
| A5   | 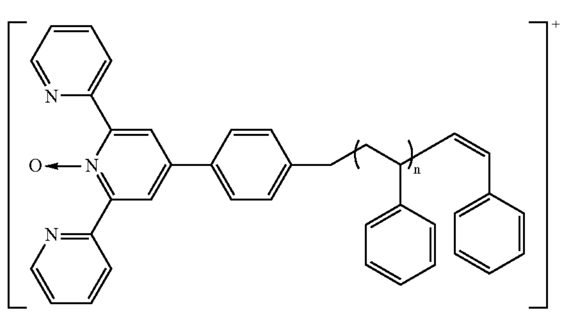          | 22 | 2730.56 | 2729.14 |
| B    | 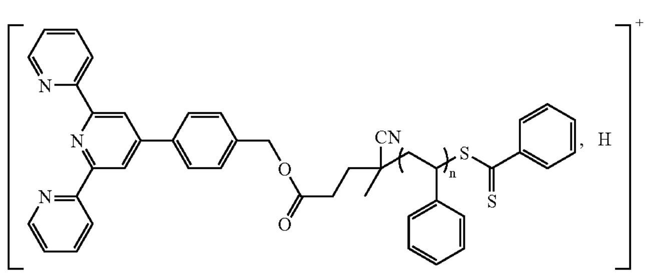          | 20 | 2682.43 | 2683.00 |

TABLE 1-continued

Assignment of peaks in the MALDI-TOF-MS spectrum (FIG. 3a) of the RAFT-prepared polystyrene PS-1 obtained using dithranol as a matrix in absence of cationic agents: calculated molar mass of the monoisotopic peak (first peak of the isotopic distribution) for the various possible structures and comparison with the experimental values.

| Peak | Structure | n | Calcd | Exptl |
|---|---|---|---|---|
| C | (structure) | 17 | 2693.38 | 2693.07 |
| D | (structure) | 8 | 2678.11 | 2678.02 |
| E | (structure) | 19 | 2747.51 | 2747.11 |

TABLE 2

Assignment of peaks in the MALDI-TOF-MS spectrum (FIG. 4a) of the RAFT-prepared polystyrene PS-2 obtained using α-cyano-4-hydroxycinnamic acid as a matrix in absence of cationic agents: calculated molar mass of the monoisotopic peak (first peak of the isotopic distribution) for the various possible structures and comparison with the experimental values.

| | | | molar mass of the monoisotopic peak (u) | |
|---|---|---|---|---|
| Peak | Structure | n | Calcd | Exptl |
| A1' | 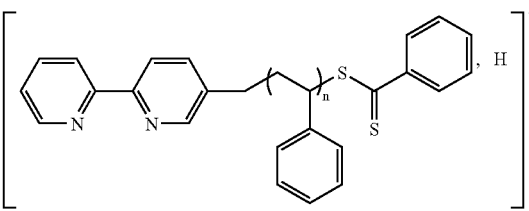 | 10 | 1363.69 | 1363.72 |
| A2' | 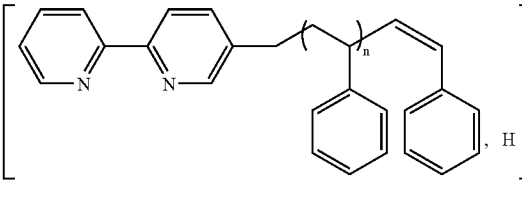 | 10 | 1313.77 | 1313.81 |
| A3' | 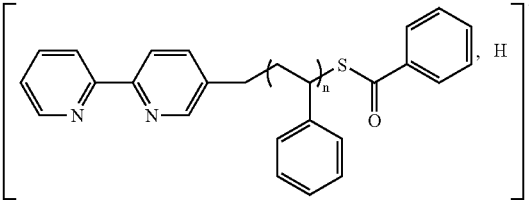 | 10 | 1347.72 | 1347.76 |
| B' | 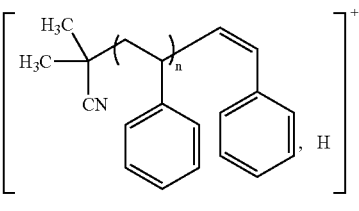 | 11 | 1316.80 | 1317.83 |
| C' | 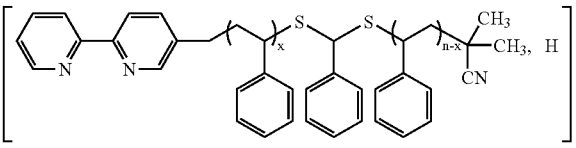 | 9 | 1328.69 | 1327.82 |

TABLE 2-continued

Assignment of peaks in the MALDI-TOF-MS spectrum (FIG. 4a) of the RAFT-prepared polystyrene PS-2 obtained using α-cyano-4-hydroxycinnamic acid as a matrix in absence of cationic agents: calculated molar mass of the monoisotopic peak (first peak of the isotopic distribution) for the various possible structures and comparison with the experimental values.

| Peak | Structure | n | molar mass of the monoisotopic peak (u) Calcd | molar mass of the monoisotopic peak (u) Exptl |
|---|---|---|---|---|
| D' | 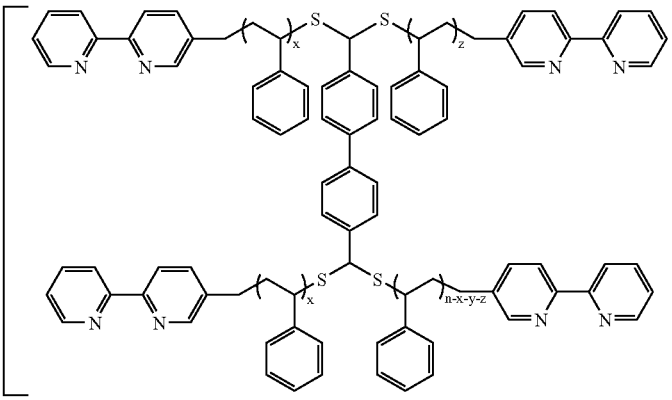 | 4 | 1399.53 | 1398.77 |
| E' | 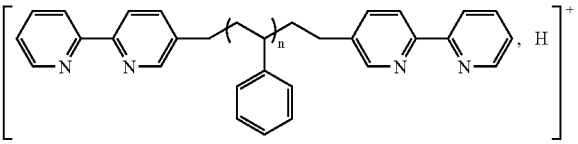 | 10 | 1379.79 | 1377.78 |

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:
1. A compound of the formula II

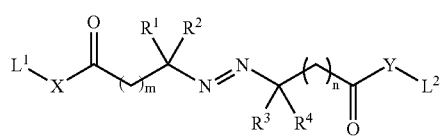

wherein $L^1$ and $L^2$ are, independently, a substituted or unsubstituted bipyridine group, tripyridine group, or phenanthroline group;
$R^1$ and $R^3$ are a $C_1$-$C_4$ alkyl group;
$R^2$ and $R^4$ are a cyano group;
X and Y are, independently, O or NH; and
m and n are 2 or 3.

2. The compound of claim 1, wherein $L^1$ and $L^2$ are, independently

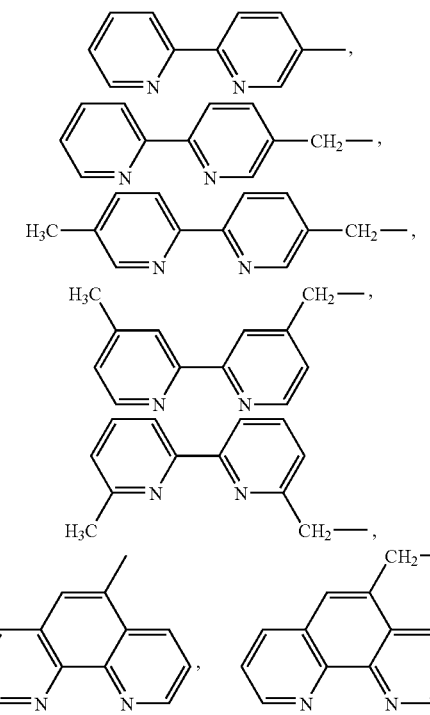

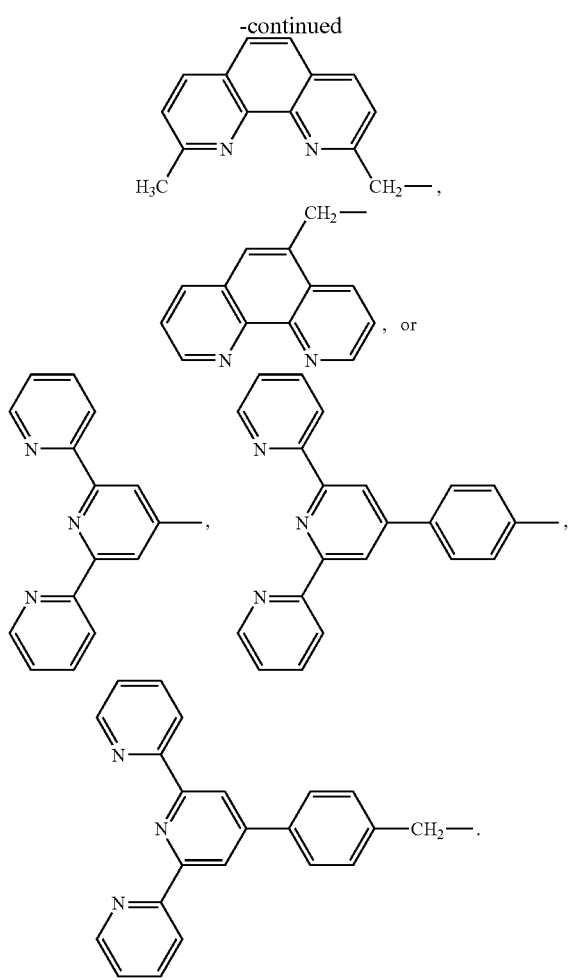
3. The compound of claim 1, wherein the compound has the formula III
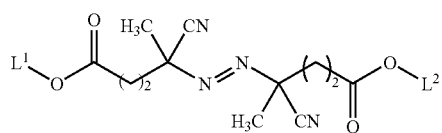
wherein L¹ and L² are
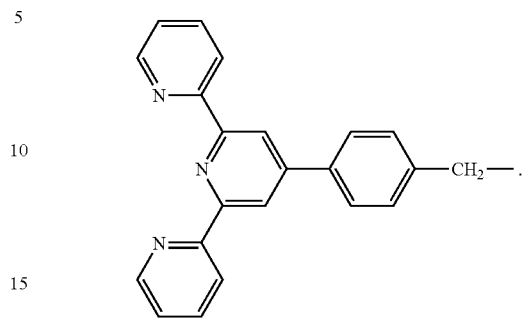
4. The compound of claim 1, wherein the compound has the formula IV
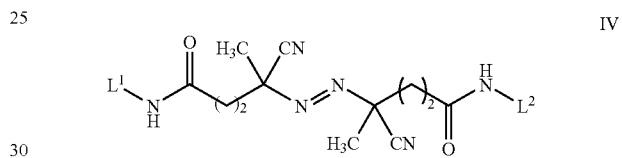
wherein L¹ and L² are
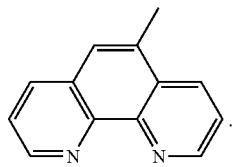
5. A method for producing a polymer, comprising heating a mixture of one or more ethylenically unsaturated monomers, a chain transfer agent, and the compound of claim 1.
* * * * *